(12) United States Patent
Buckley et al.

(10) Patent No.: US 10,136,978 B2
(45) Date of Patent: Nov. 27, 2018

(54) DOSING APPARATUS (71) Applicant: Imaginus Limited, Chatswood, North Shore (NZ)

(72) Inventors: Paul Fleming Buckley, Auckland (NZ); Robert William Lachlan Holmes, North Shore (NZ); Malcom Norman Lynd, Auckland (NZ)

(73) Assignee: Imaginus Limited (NZ)

( * ) Notice: Subject to any disclaimer, the term of this patent is extended or adjusted under 35 U.S.C. 154(b) by 90 days.

(21) Appl. No.: 14/908,479

(22) PCT Filed: Aug. 7, 2014

(86) PCT No.: PCT/NZ2014/000162
§ 371 (c)(1),
(2) Date: Jan. 29, 2016

(87) PCT Pub. No.: WO2015/020539
PCT Pub. Date: Feb. 12, 2015

(65) Prior Publication Data
US 2017/0000594 A1 Jan. 5, 2017

(30) Foreign Application Priority Data

Aug. 7, 2013 (NZ) ...................... 614052

(51) Int. Cl.
*A61D 7/00* (2006.01)
*A61D 1/02* (2006.01)
*A61M 5/00* (2006.01)

(52) U.S. Cl.
CPC ................ *A61D 7/00* (2013.01); *A61D 1/02* (2013.01); *A61M 2005/005* (2013.01)

(58) Field of Classification Search
CPC ......... A61D 7/00; A61D 1/02; A61M 5/2448; A61M 2005/2403; A61M 2005/2407; A61M 2005/2411; A61M 2005/2414; A61M 2005/005; B65G 57/16; B65G 57/165; B65G 57/18; B65G 57/183; B65G 57/186
See application file for complete search history.

(56) References Cited

U.S. PATENT DOCUMENTS

| | | | | |
|---|---|---|---|---|
| 4,077,406 A | * | 3/1978 | Sandhage | A61M 37/0069 604/61 |
| 4,400,170 A | * | 8/1983 | McNaughton | A61M 37/0069 604/61 |
| 4,447,223 A | * | 5/1984 | Kaye | A61M 37/0069 604/61 |
| 4,518,384 A | * | 5/1985 | Tarello | A61M 5/20 604/61 |

(Continued)

*Primary Examiner* — Nathan R Price
*Assistant Examiner* — Dung Ulsh
(74) *Attorney, Agent, or Firm* — Skinner and Associates; Joel Skinner (57) ABSTRACT

Dosing apparatus comprising a cartridge (11), the cartridge having: •a body (13) with a cavity holding at least one product to be dosed, •a nozzle (17) which is in communication with the cavity and which is configured for channelling the product to an orifice of an animal, and •a recess (21) which is adapted to, or actually does, receive and provide a cover for the nozzle of an identical or similar cartridge.

21 Claims, 13 Drawing Sheets

(56) References Cited

U.S. PATENT DOCUMENTS

| | | | | |
|---|---|---|---|---|
| 4,673,387 A | * | 6/1987 | Phillips | A61M 37/0069 |
| | | | | 604/62 |
| 4,787,384 A | * | 11/1988 | Campbell | A01K 11/006 |
| | | | | 604/60 |
| 5,522,797 A | * | 6/1996 | Grimm | A61M 37/0069 |
| | | | | 604/61 |
| 6,446,578 B1 | * | 9/2002 | Irwin | A61D 7/00 |
| | | | | 119/604 |
| 6,551,819 B1 | | 4/2003 | Simmet | |
| 6,588,612 B1 | * | 7/2003 | Dorn | B65D 1/18 |
| | | | | 206/509 |
| 9,302,809 B1 | * | 4/2016 | Hooper | B65D 25/2826 |
| 9,750,879 B2 | * | 9/2017 | Solomon | A61M 5/2033 |
| 2006/0219593 A1 | * | 10/2006 | Linz | B65D 21/0223 |
| | | | | 206/509 |
| 2007/0114200 A1 | * | 5/2007 | Lane | B65D 1/023 |
| | | | | 215/10 |
| 2011/0204051 A1 | * | 8/2011 | Pawl | B65D 21/0202 |
| | | | | 220/23.83 |
| 2013/0213846 A1 | * | 8/2013 | Hendrickson | B65D 21/0216 |
| | | | | 206/509 |

\* cited by examiner

DOSING APPARATUS

FIELD OF THE INVENTION

This invention relates to a dosing apparatus. A particularly preferred form of the invention relates to a cartridge for use with a dispenser, for dosing therapeutic and preventative agents into the teat canal of cows udders.

BACKGROUND

Mastitis is a significant animal health problem affecting global dairy production. Dosing a heard of dairy cows to treat or protect against mastitis can be a very labour intensive exercise. For example, the organisation Dairy NZ suggests a treatment procedure estimated to take approximately 3 minutes per cow. It is important that scrupulous hygiene is observed to ensure the treatment is successful. But with an average time of 3 minutes, it means that to give blanket dry cow treatment to all cows in the average New Zealand herd of say 400 cows, over 20 hours of time would be expended. This indicates just how time consuming the process can be. The problem can be accentuated in cases where a new dosing syringe has to be obtained and manipulated for each cow.

A further issue with treating cows for mastitis is that the equipment used should be scrupulously clean. It should not itself present a source of bacterial contamination. However with many know dosing syringes it is necessary to remove a cover cap by hand each time a cow is dosed. This presents an opportunity for bacterial infection to pass to the syringe, and therefore to the cows.

Another issue is that often farmers wish to administer an antibiotic paste into the teat canal followed by a teat sealant during the same treatment occasion. With some known techniques this can require farmers to administer 8 syringes per cow, or 2400 syringes in an average sized New Zealand herd.

It is an object of a preferred embodiment of the present invention to provide a dosing apparatus which goes at least some way towards overcoming one or more of the above problems. While this object applies to a preferred embodiment, it should not be seen as a limitation on the scope of the invention as claimed. The object of the invention per se is simply to provide the public with a useful choice.

The term "comprising" or derivatives thereof (eg "comprises"), if and when used herein, should be interpreted non-exclusively—eg if used in relation to a specific combination of features it should not be taken to exclude the possibility of there also being additional unspecified features.

INTERPRETATION

The terms "comprising" and "comprises", or similar, if and when used herein, should not be interpreted exclusively. When used in relation to a combination of features they should not be taken to exclude the option of there being further unspecified features.

SUMMARY OF THE INVENTION

According to one aspect of the invention there is provided dosing apparatus comprising a cartridge, the cartridge having:
 a body with a cavity holding at least one product to be dosed,
 a nozzle (eg a cannula) which is in communication with the cavity and which is configured for channelling the product to an orifice of an animal, and
 a recess which is adapted to, or actually does, receive and provide a cover for the nozzle of an identical or similar cartridge.

Optionally the recess seals the nozzle of the second mentioned cartridge.

Optionally the nozzle comprises a tubular section sized to fit within the teat orifice of a dairy cow.

Optionally wherein the nozzle of the second mentioned cartridge includes a resilient collar section at a base thereof which is in sealing contact with a complimentary shaped portion of the recess of the first mentioned cartridge.

Optionally the nozzle is at an angle to the body of 70°-90° (preferably approximately) 90°).

Optionally the cavity is cylindrical.

Optionally each cartridge has at least one piston configured to push the product from its cavity.

Optionally each cartridge has a first piston configured to expel the product from its cavity, and a second piston configured to expel a second product from the cavity.

Optionally each cartridge is configured to expel the first mentioned product through the nozzle, and, only after that, to expel the second mentioned product such that it flows past the first piston and exits the cartridge via the nozzle.

Optionally the cavity of each cartridge is configured to allow the second product to flow past the first piston when the first piston has travelled to the limit of its range of travel after dispensing the first mentioned product.

Optionally the cavity of each cartridge includes a section having a greater cross sectional area at the location where the first piston sits when it has travelled to the limit of its range after dispensing the first mentioned product.

Optionally the cavity of each cartridge includes a section having a reduced radius at a location where the first piston sits when it has travelled to the limit of its range of travel after dispensing the first mentioned product.

Optionally the first piston of each cartridge has a unidirectional seal which is configured to prevent the first mentioned product from travelling past the first piston and toward the second piston and to allow the second mentioned product to flow past the first piston.

Optionally the dosing apparatus incorporates a dispenser loaded with the cartridges and adapted to dispense product from each cartridge, one after the other.

Optionally the dispenser comprises a hand held dispenser gun.

Optionally there are at least 3 of the cartridges loaded in the dispenser.

Optionally the dispenser has a plunger arranged to drive the piston(s) of one of the cartridges before the piston(s) of another of the cartridges.

Optionally the dispenser has a magazine which receives the cartridges in a stack, the magazine having a spring which biases the cartridges towards a breach of the dispenser for engaging the plunger.

Optionally the dispenser incorporates a squeeze handle for powering movement of the plunger and has a spring for biasing the handle to a non-squeezed disposition.

Optionally the dispenser has a slide which prevents one of the cartridges, which is in the breach, from being released from the dispenser until that cartridge has had its contents expelled via its nozzle.

Optionally the slide is automatically withdrawn during a reloading sequence of the dispenser.

Dosing apparatus according to any one of the preceding claims, having a piece which moves with, or as part of, a/the plunger to push between the cartridges and assist in separating them when one of the cartridges in the a/the breach has been used.

Optionally the dosing apparatus is arranged to push a plunger thereof to dispense product from the cartridges one after the other and wherein the plunger is:
hand powered;
pneumatically powered;
electrically powered; or
hydraulically powered.

DESCRIPTION OF THE DRAWINGS

Some preferred forms of the invention will now be described by way of example and with reference to the accompanying drawings, of which.

DETAILED DESCRIPTION

With reference to FIGS. 1 to 8, a first example of a dosing cartridge (11) according to the present invention will now be described. The dosing cartridge (11) has a body (13) with a cavity (15) for holding a product to be dosed. The dosing cartridge (11) also has a nozzle in the form of a cannula (17) which is in communication with the cavity (15), and which is configured for channelling the product within the cavity (15) into an orifice of an animal.

The dosing cartridge (11) is designed for use with a dispenser gun (19), and is primarily intended for dosing small quantities of antibiotic paste and/or teat sealant material into the teat canals of the udders of cows or similar milk producing animals.

Figure 1:
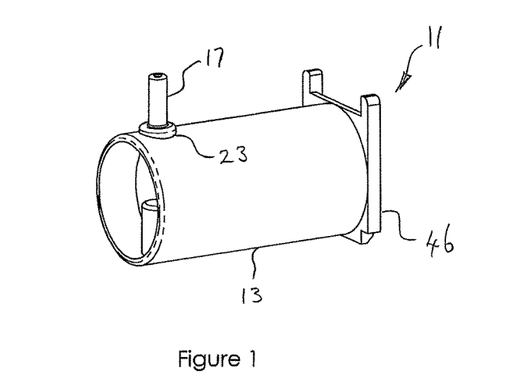
FIG. 1 is a perspective view of a dosing cartridge for use with a dispenser gun.
Figure 2:
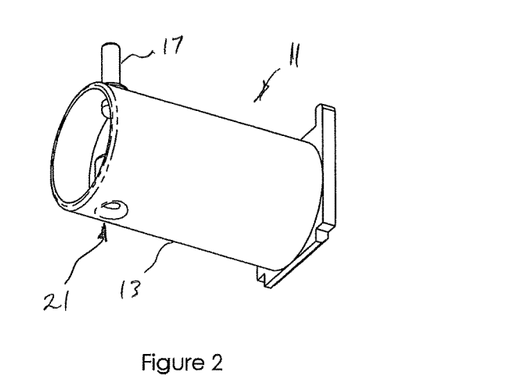
FIG. 2 is an alternative perspective view of the dosing cartridge.

A unique feature of the cartridge (11) is that it includes a sealing recess (21) that is configured for use as a sealing cap for the nozzle (17) of a similarly configured dosing cartridge (11). It can be seen that the nozzle (17) comprises a short tube. The nozzle (17) is about six to eight millimeters long, a diameter of about two to three millimeters and is sized to fit within the teat canal of a dairy cow. The recess (21) comprises a cylindrical hole, and short length of tube closed at its innermost end, both sized to fit over the nozzle of an adjacent cartridge with a slight interference fit. In this way, the nozzle (17) of an adjacent cartridge (11) can be kept clean prior to use of the adjacent cartridge (11). The nozzle (17) also includes a collar section (23) at a base of the nozzle (17) configured to mate in sealing contact with a correspondingly shaped tapered portion of the sealing recess (21) of a similarly configured dosing cartridge (11).

Figure 3:
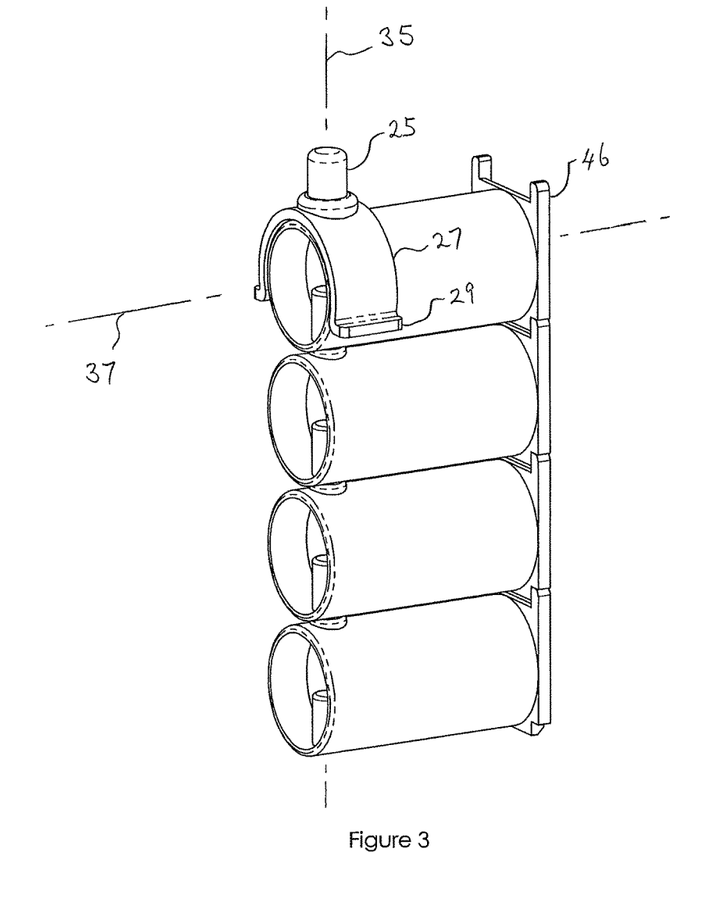
FIG. 3 is a perspective view showing a stack of four of the dosing cartridges in an assembled state.
Figure 4:
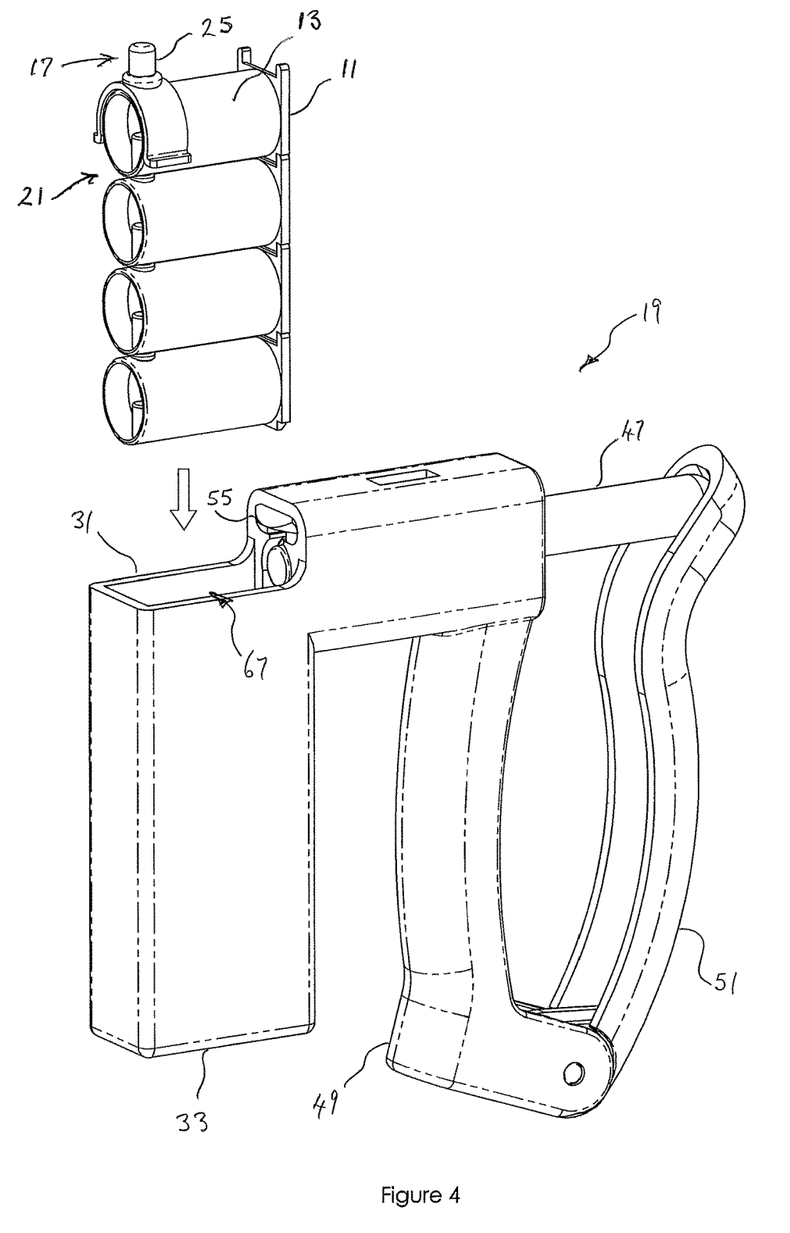
FIG. 4 is a perspective view showing the stack of cartridges about to be fitted into the magazine of a dispenser gun.
Figure 5:
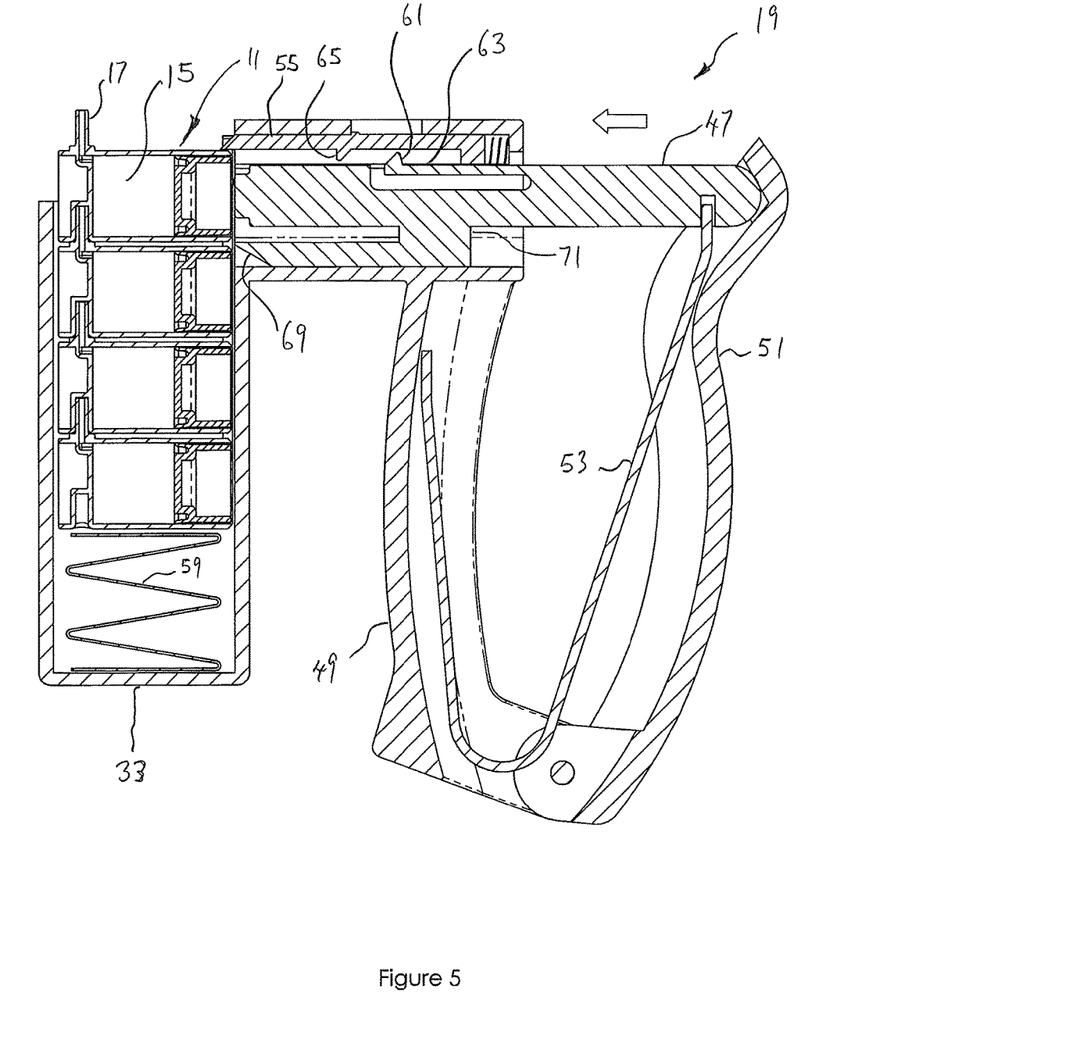
FIG. 5 is a cross sectional view of the dispenser gun with the stack of cartridges in the magazine.

With reference to FIG. 3 it can be seen that when four of the cartridges (11) are stacked, the nozzles (17) of three of the cartridges (11) are covered by the recess (21) of the respective adjacent cartridge (11). A separate cap (25) is provided for the nozzle (17) of the top cartridge (11). In this example the cap (25) includes a "C" shaped clamp (27) which is used to hold it onto the cartridge body (13). The cap (25) also includes wings (29) which extend outwardly from each side of the clamp (27) and which are configured to contact a top edge (31) of a magazine (33) of the dispenser gun (19). When the assembled stack of four cartridges is inserted into the magazine (33), the wings (29) will contact the top edge (31) of a magazine (33) and in this way the cap (25) will automatically be pushed from the nozzle (17) of the top cartridge (11), minimising the possibility of accidentally touching the nozzle (17) and contaminating it during cap (25) removal.

Referring to FIG. 2, a helpful feature of the cartridge (11) is that the principal longitudinal axis (35) of the nozzle (17) is at an angle to the principal longitudinal axis (37) of the body section (13). Ideally the longitudinal axis (35) of the nozzle is at an angle of between seventy and ninety degrees to the longitudinal axis (37) of the body section (13), and in this example the axis (35) of the nozzle is at an angle of about ninety degrees to the axis (37) of the body section (13).

Figure 6:
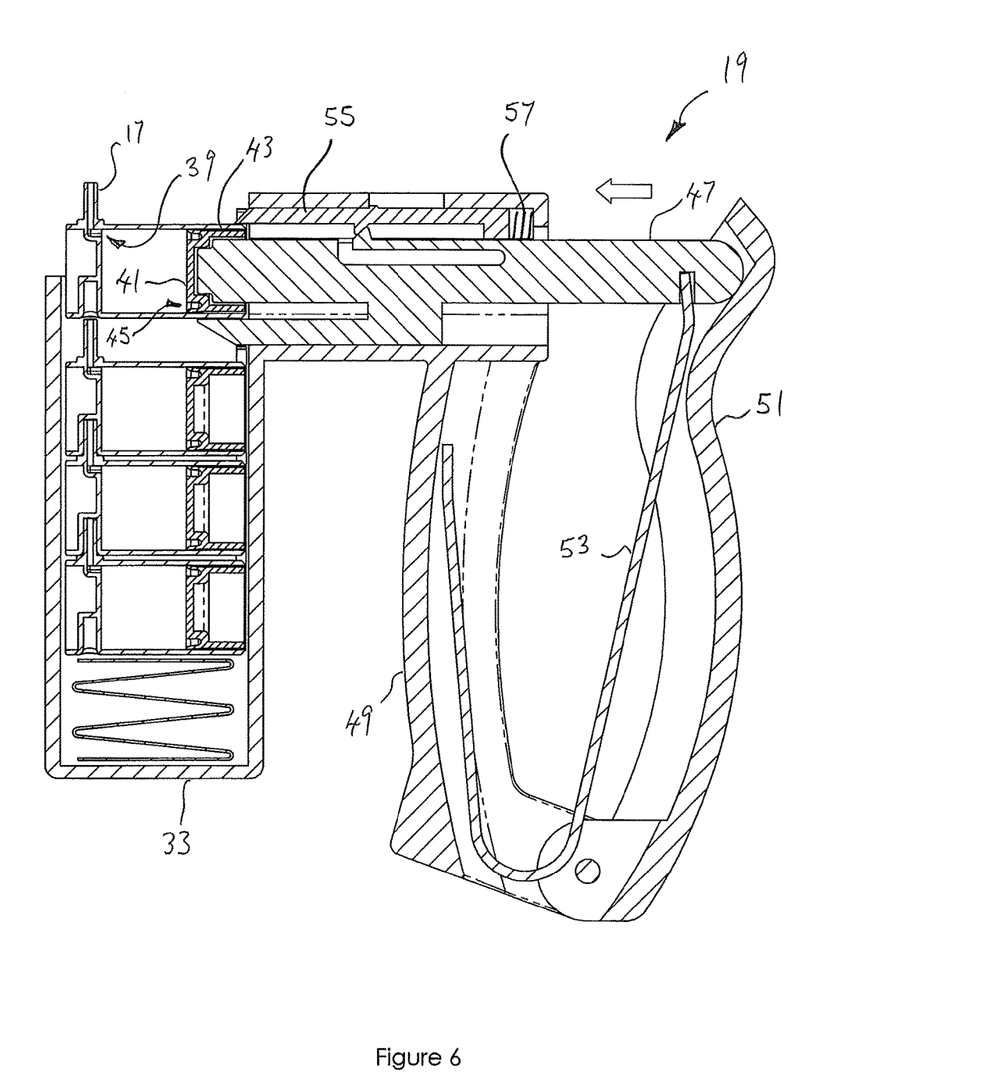
FIG. 6 is a further cross sectional view of the dispenser gun and stack of cartridges, during a dispensing action.
Figure 7:
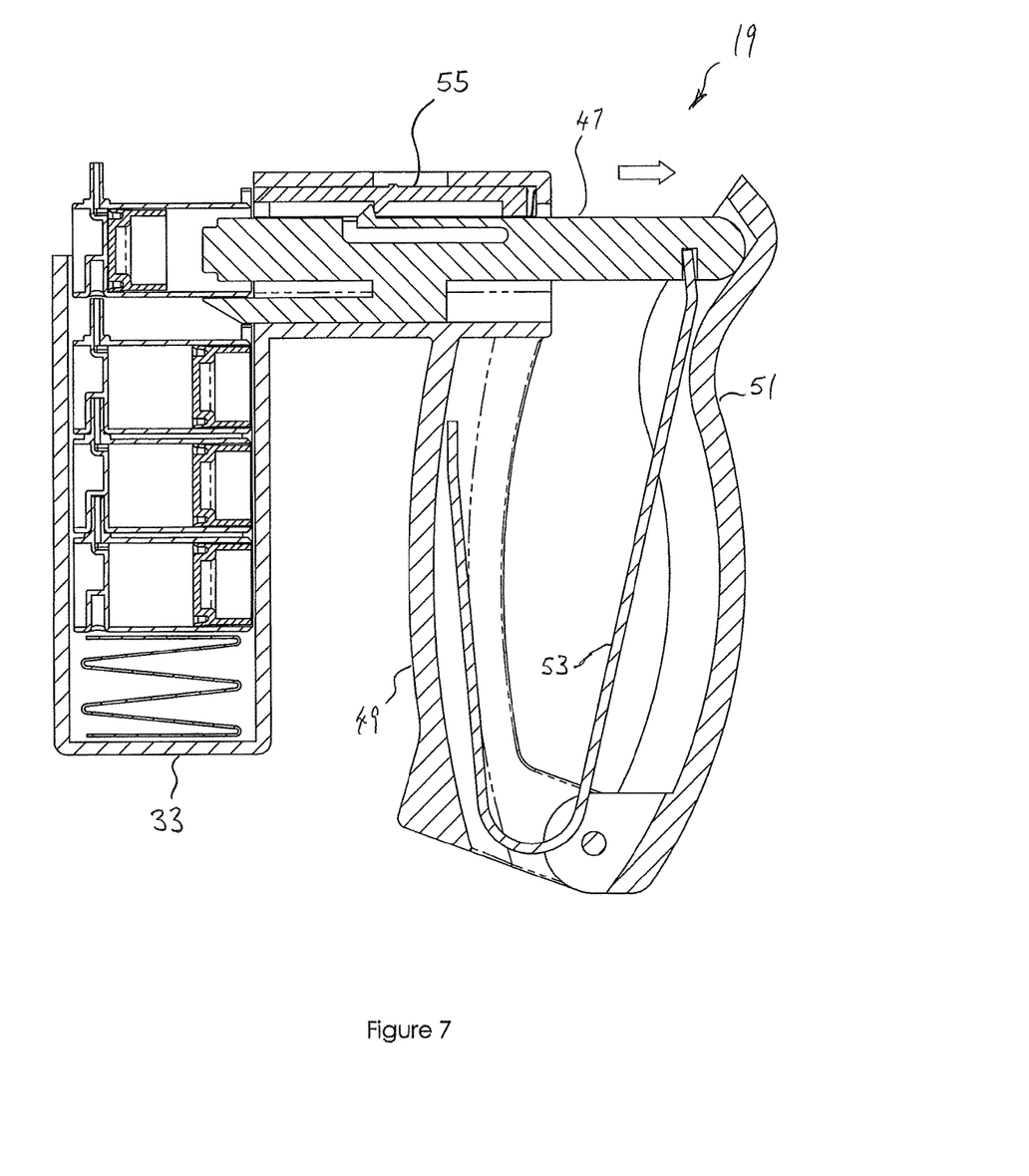
FIG. 7 is a cross sectional view of the of the dispenser gun and stack of cartridges, showing a plunger being withdrawn after expelling the contents of the top cartridge.
Figure 8:
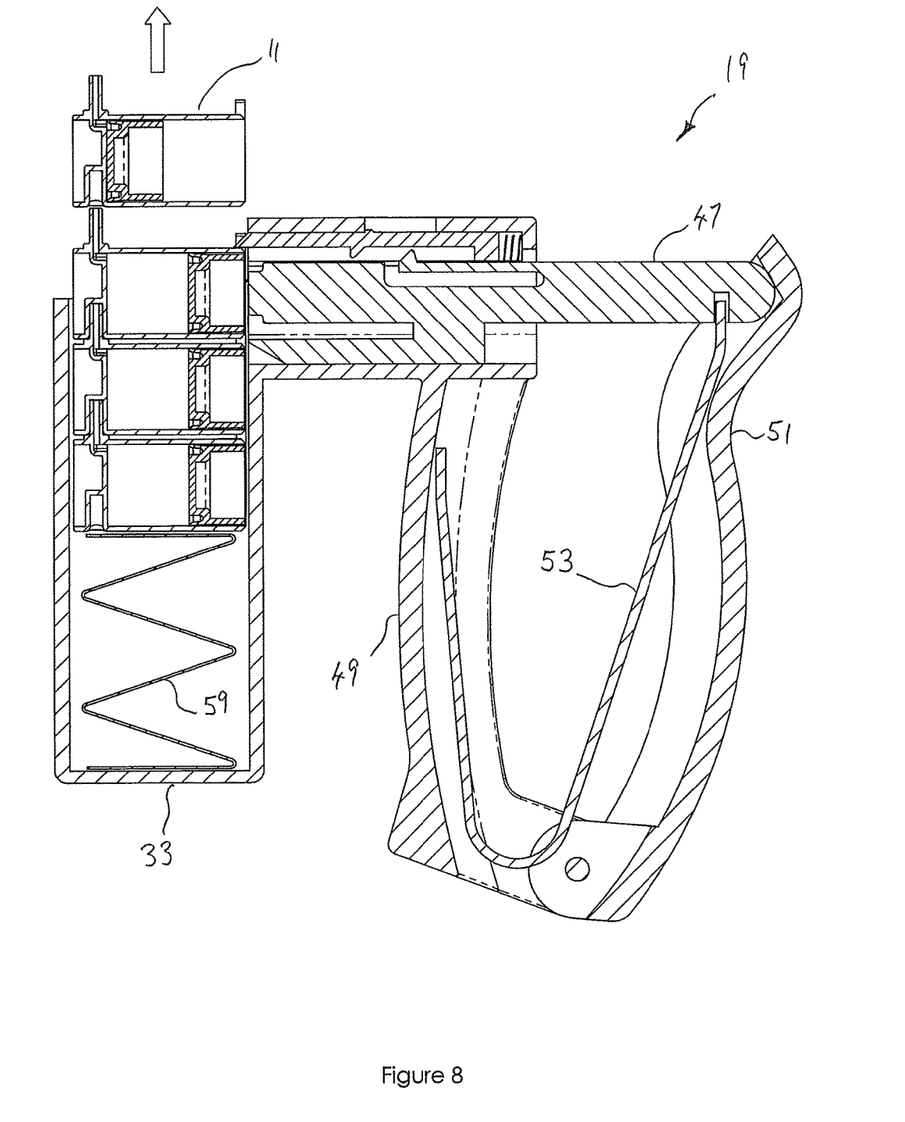
FIG. 8 is a cross sectional view of the of the dispenser gun and stack of cartridges, showing the first cartridge being ejected and the remaining cartridges being pushed upwards within the magazine.

This right angled configuration of the nozzle (11) allows the user of the dispenser gun (19) and cartridges (11) to apply the dose of product vertically upwards and into the teat canals without unduly twisting his of her hands to orientate the nozzle (11) to suit the orientation of the teats. It can be seen that in this example that the cavity (15) of the body (13) is cylindrical, and that the longitudinal axis of the cylindrical shaped cavity (15) is aligned with the longitudinal axis (37) of the body section (13). Referring to FIG. 6, a short passage (39) connects the inner end of the cylindrical shaped cavity (15) with the nozzle (17). The dosing cartridge (11) also includes a piston (41). In this example the piston has piston skirts (43) which keep the piston (41) aligned with the cylindrical shaped cavity (15). The piston (41) also includes a cup seal (45) about its periphery. The forward end of the cup seal (45) faces the product within the cartridge (11). For this reason, as the piston (41) is pushed further into the cylindrical shaped cavity (15), the pressure within the product acts to push the outer lips of the cup seal (45) outwards to help maintain a seal between the piston and the inner wall of the cylindrical shaped cavity (15).

It can also be seen in the figures that each cartridge (11) includes a substantially square interlocking tab (46) at the end opposite the end having the nozzle (17). The tabs (46) are configured to facilitate interlocking between adjacent cartridges (11), and the straight sides of the interlocking tabs (46) help to keep the cartridges (11) aligned when situated within the magazine (33).

With reference to FIGS. 4 to 8 it can be seen that the dispenser gun (19) includes a plunger (47) for engaging with, and pushing, the piston (41) to dispense product held within the dosing cartridges (11). The magazine (33) of the dispenser gun (19) holds the four dosing cartridges (11) and presents them to the plunger (47) one after the other.

A handle (49) of the dispenser gun (19) includes a lever style trigger mechanism (51) which is configured to push the plunger (47) when the handle (49) is squeezed by hand. A spring (53) returns the trigger (51) and plunger (47) to a withdrawn position when a hand squeeze action is relaxed.

The dispenser gun (19) also includes a cartridge retaining means or latch in the form of a movable slide (55). The slide (55) is normally held in an extended position by a latch spring (57). In the extended position, the slide (55) extends into the path of the cartridges (11) which are situated in the magazine (33) and which are urged upwards within the magazine by a magazine spring (59). In this extended position, the slide (55) prevents cartridges (11) from exiting the magazine.

The plunger (47) includes a barb (61) situated on a flexible arm (63). The barb (61) is configured to catch on a corresponding slide barb (65) when the plunger (47) is moving back to its withdrawn position during a cartridge reloading sequence. When the plunger barb (61) catches on the slide barb (65), the plunger (47) momentarily retracts or withdraws the slide (55) and allows the spent cartridge (11) to be ejected. Continued withdrawal of the plunger (47) causes the plunger barb (61) to detach from the slide barb (65) and to allow the slide (55) to return to its extended position under the action of the latch spring (57). During this sequence the magazine spring (59) loads the next cartridge (11) into the breach (67) of the dispenser gun (19).

The dispenser gun (19) also includes a cartridge separating means configured to separate adjacent cartridges (11) from one another. The cartridge separating means is in the form of a wedge shaped blade (69) that runs parallel to the plunger (47) and is physically connected to the plunger (47) by a short arm (71). When the plunger (47) is advanced to push product from the cartridge (11) that is situated within the breach (67), the blade (69) advances at the same time. The blade (69) is aligned with the joint between the cartridge (11) that is in the breach (67) and the cartridge (11) immediately below it. As the blade (69) advances the wedge shape of the blade (69) causes the two cartridges (11) to separate, facilitating release of the nozzle (17) of the lower cartridge (11) from the sealing recess (21) of the upper cartridge (11). This allows the upper cartridge (11) to be ejected easily when the slide (55) is withdrawn as described above.

With reference to FIGS. 9 to 12, examples of cartridges which are configured to hold more than one product formulation will now be described. These figures show four examples of cartridges designed to hold and dispense two product formulations, one after the other, for example to dispense an antibiotic paste into the teat canal, followed by a teat sealant material. In each case, the dosing cartridge includes two pistons, a first piston configured to expel a first product from the cavity, and a second piston configured to expel a second product from the cavity. In addition, the dosing cartridges are all configured to dispense the first product through the nozzle first, and, when the first product has been dispensed, to allow the second product to flow past the first piston and be dispensed through the nozzle.

Figure 9:
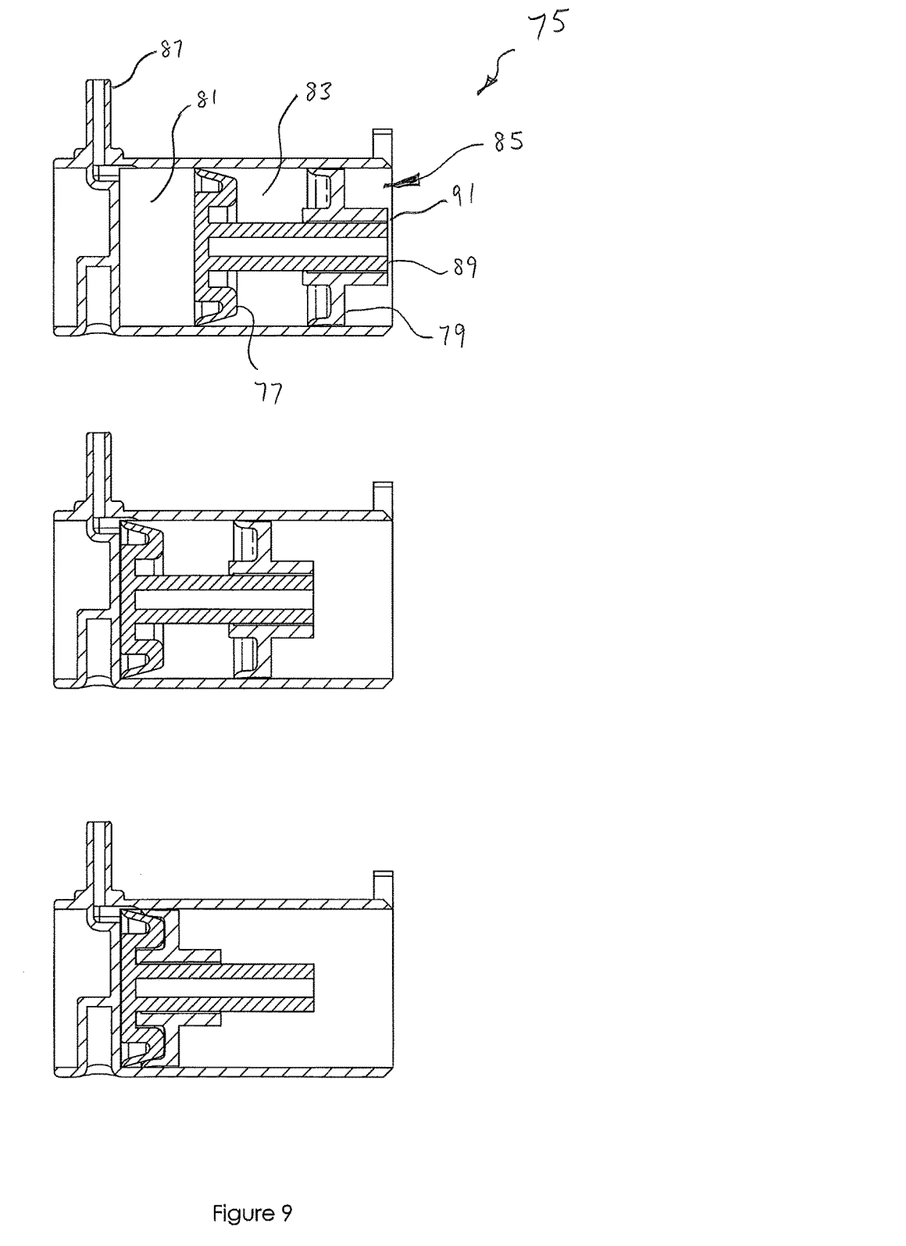
FIG. 9 is a sequence of cross sectional views of a second example of a dosing cartridge.

As shown in FIG. 9, a second example of a dosing cartridge (75) includes a first piston (77) and a second piston (79). A first compartment (81) is defined between the first piston (77) and the forward end of the cartridge cavity (85). A second compartment (83) is defined between the first piston (77), the second piston (79) and the inner diameter of the cartridge cavity.

In use, the plunger (47) pushes against the second piston (79). This causes both pistons to move and for product to be discharged from the first compartment (81). Product continues to be discharged from the first compartment (81) until the first piston (77) has travelled to the limit of its range, that is, until it butts up against the inner end of the cavity (81).

The cavity (85) is configured to allow the second product to flow past the first piston (77) when the first piston (77) has travelled to the limit of its range, as shown in the second of the views in FIG. 9. The forward end of the cavity (85) has a slightly larger diameter, or a short channel, and this slightly larger localised cross sectional area allows product from the second compartment (83) to by-pass the first piston (77), and to exit via the nozzle (87), when the first piston (77) has contacted the inner end of the cavity (85). Product continues to be discharged from the second compartment (83), and out through the nozzle, until the second piston (79) butts up against the first piston (77).

The first piston (77) includes a central shaft (89) which engages with a bore (91) in the centre of the second piston (79). The central shaft (89) helps to stabilise the first piston (77) and to prevent it skewing within the cavity (85). In this example, the central shaft (89) has a sealing fit with the bore (91).

It could also be said that the first piston (77) includes a uni-directional seal, that is a cup seal, which is configured to prevent the first product from travelling past the first piston (77) and toward the second piston (79), but which will allow the second product to flow past the first piston (77) when the first piston (77) butts up against the inner end of the cavity (85), as shown in the second of the views in FIG. 9.

Figure 10:
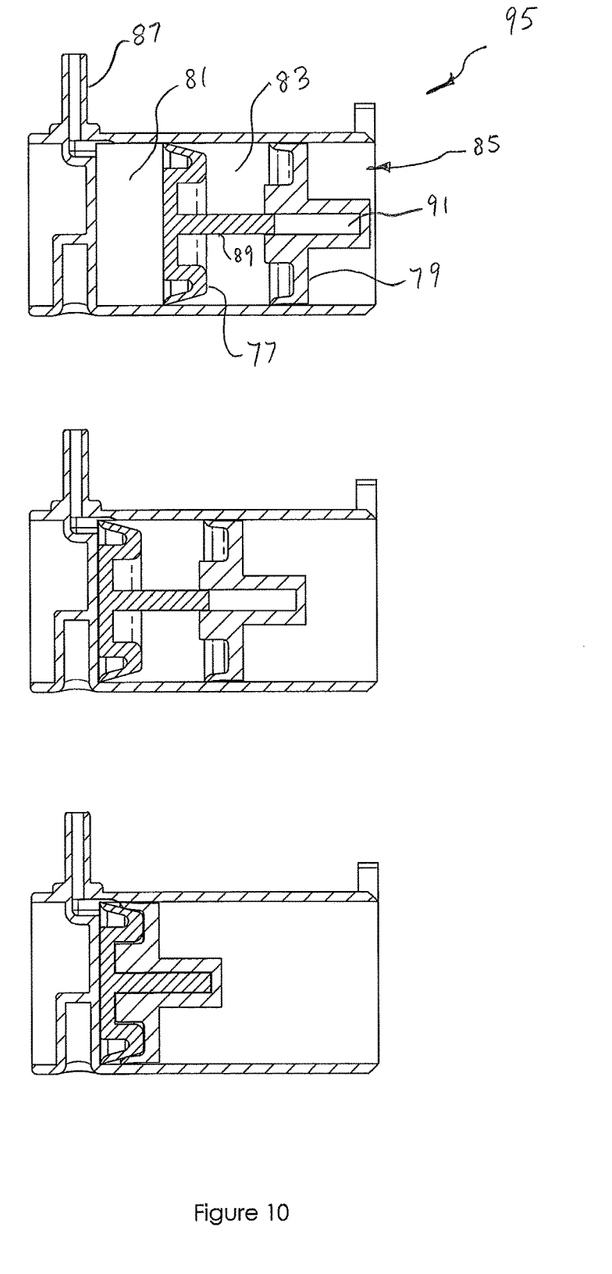
FIG. 10 is a sequence of cross sectional views of a third example of a dosing cartridge.

A third example of a dosing cartridge (95) is shown in FIG. 10. The third example of a dosing cartridge (95) is similar to the second example except that the bore (91) has a closed end, eliminating the need for the sealing fit between the central shaft (89) and the bore (91).

Figure 11:
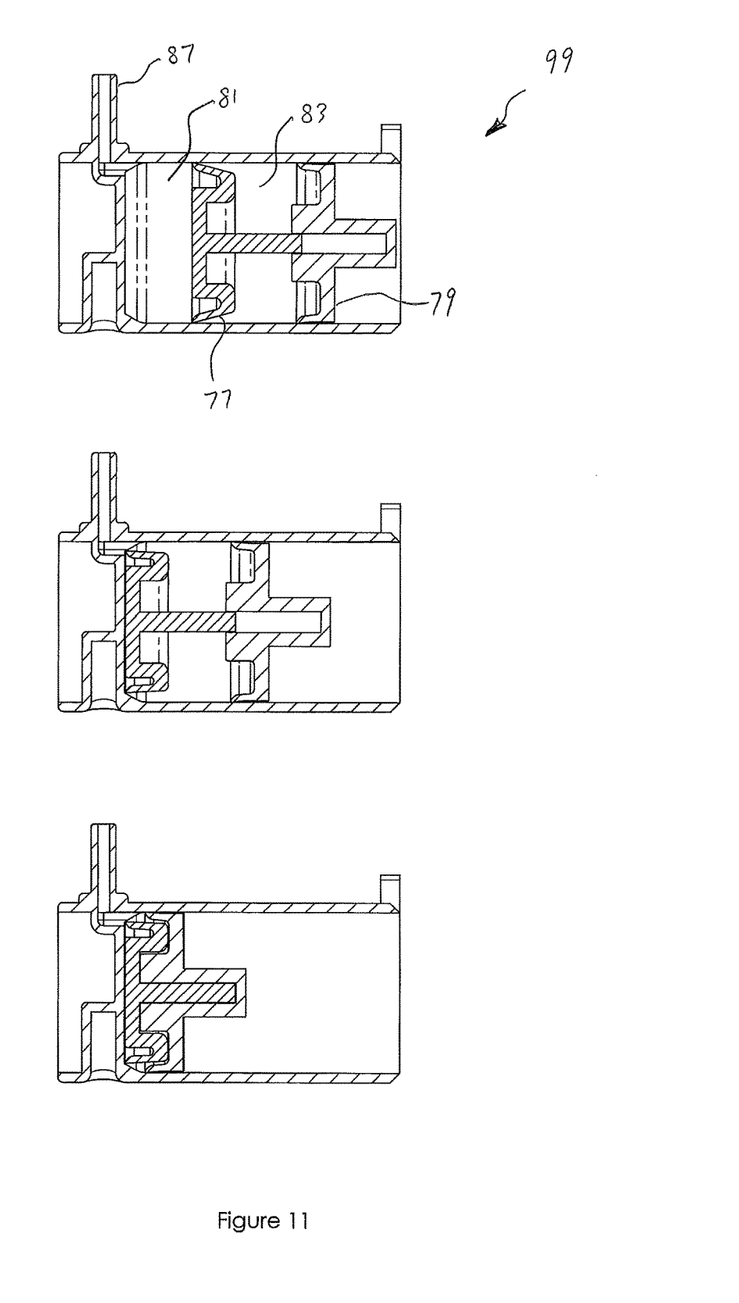
FIG. 11 is a sequence of cross sectional views of a fourth example of a dosing cartridge.

A fourth example of a dosing cartridge (99) is shown in FIG. 11. This is similar to the third example of a dosing cartridge (95) except that instead of a larger diameter at the forward end of the cavity (85), this example has a reduced radius which causes the lips of the cup seal about the periphery of the first piston (77) to collapse inwards, allowing product from the second compartment (83) to by-pass the first piston (77), and to exit via the nozzle (87), when the first piston (77) has contacted the inner end of the cavity (85).

Figure 12:
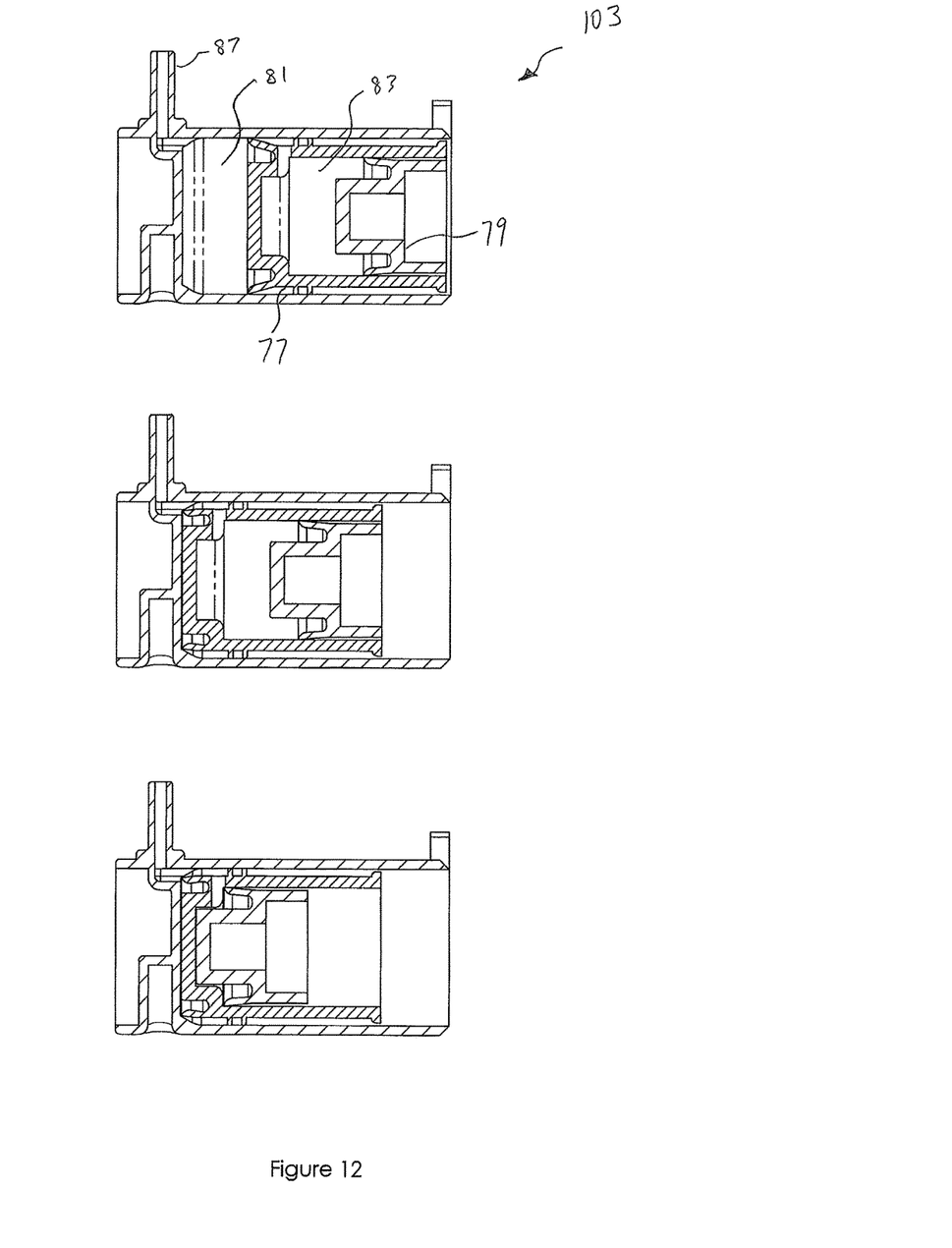
FIG. 12 is a sequence of cross sectional views of a fifth example of a dosing cartridge.

A fifth example of a dosing cartridge (103) is shown in FIG. 12. This is similar to the fourth example of a dosing cartridge (99) except that the first piston (77) includes a skirt to help keep it stable within the cavity, and it no longer includes a central shaft. In addition, the second piston (79) has a reduced diameter and fits within the skirt of the first piston (77). Also, the skirt of the first piston (77) is provided with at least one transfer orifice which allows product to be transferred from within the second compartment (83) to the outside diameter of the first piston (77) and then past the seal of the first piston (77) and toward the nozzle (87).

Each of these dosing cartridges (75), (95), (99) and (103) can be used in place of the first dosing cartridge (11) in the dosing apparatus (19) subject to appropriate modifications of the forward end of the plunger (47) to achieve the required engagement between the second piston (79) of each cartridge. For example, the centre of the forward end of the plunger (47) will require an appropriately sized hole, when used with the second cartridge (75), to allow engagement with the second piston (79) only, and to allow the plunger (47) to push the second piston (79) toward the first piston (77) without contacting the central shaft (89) of the first piston (77).

All he examples shown and described above are designed primarily for injecting material into teat canals. It is envisaged that with minor variations the cartridges and apparatus could be used to inject products into other cavities.

In the examples described above, the dispenser gun (19) is designed to dispense four cartridges prior to reloading the magazine. It is envisaged that variations of the gun (19) could be adapted to dispense fewer or more cartridges as desired.

Figure 13:
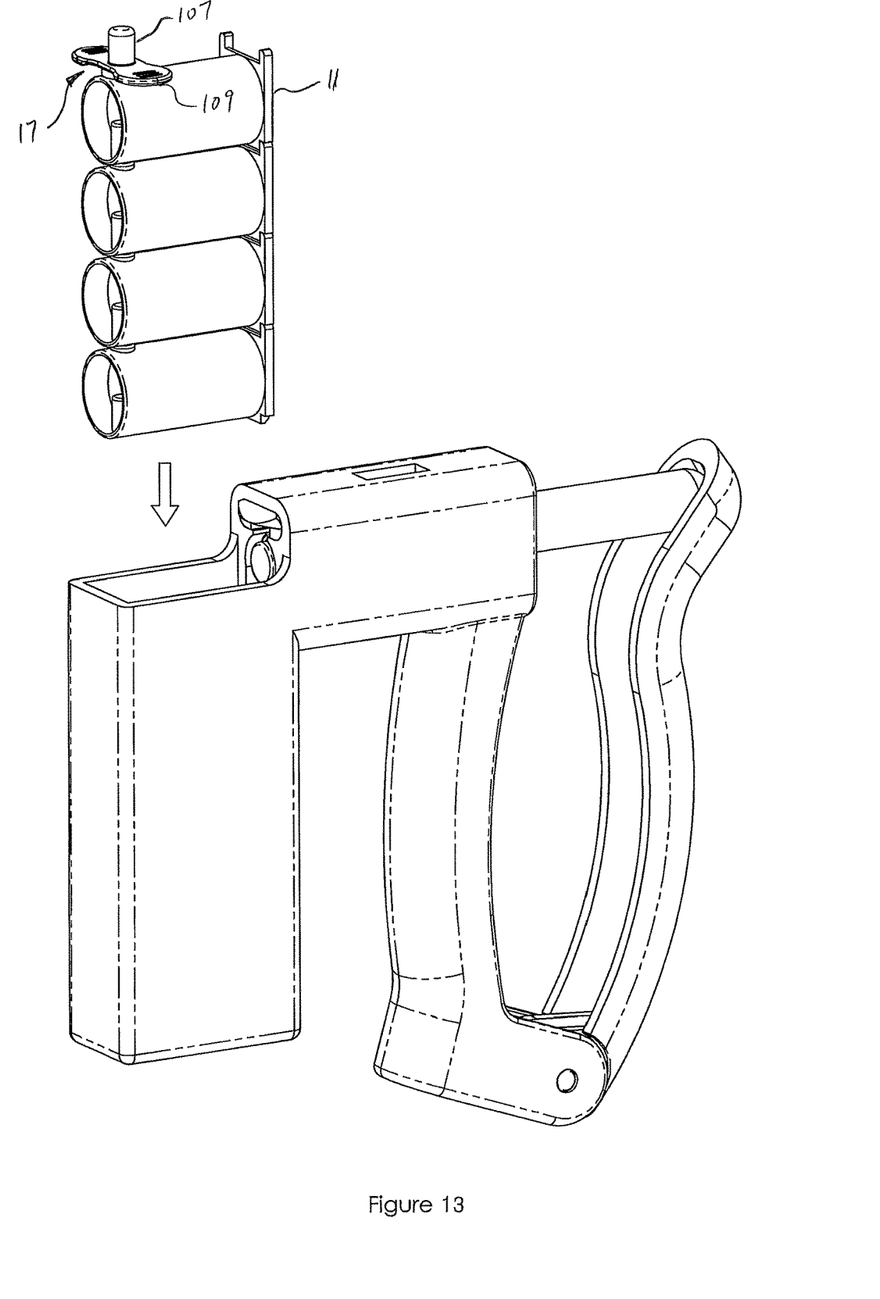
FIG. 13 is a perspective view showing a stack of four of the dosing cartridges being fitted into a magazine of a dispenser gun, the top cartridge having an alternative style of sealing cap.

With reference to FIG. 13, an alternative top sealing cap (107) is shown, the sealing cap (107) having tabs (109) which allow the cap (107) to be removed manually, for example by gripping the tab (109) with the fingers and 'tearing' the tab (109) and, therefore the cap (107) overall, from the nozzle (17) of the top cartridge (11).

Figure 14:
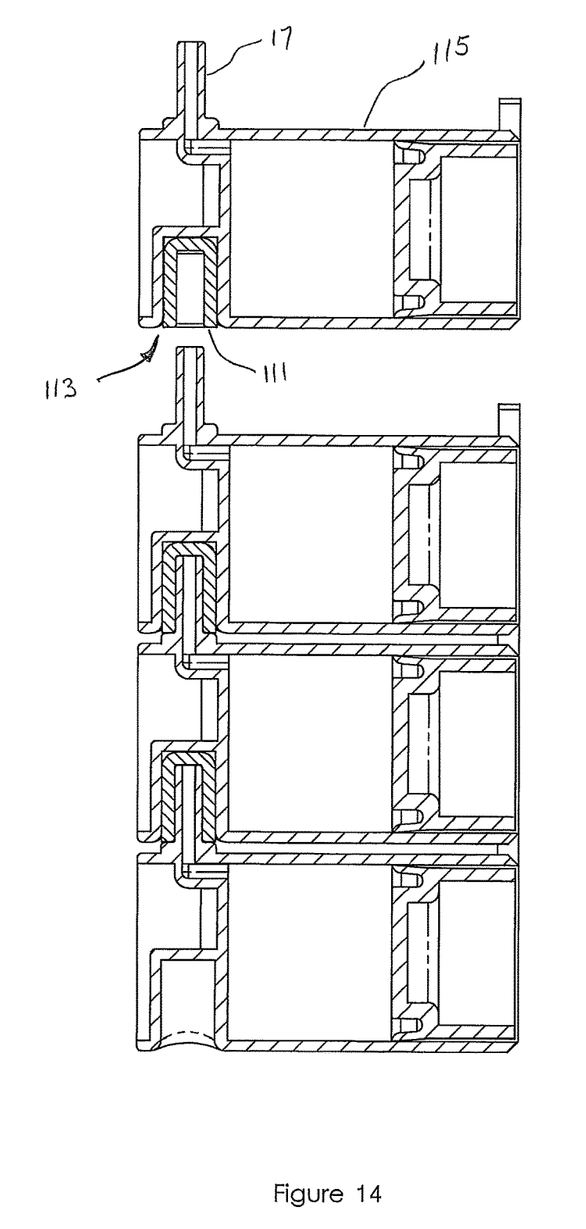
FIG. 14 is a cross sectional view of a sixth example of a dosing cartridge.

With reference to FIG. 14, an alternative sealing arrangement for the nozzles (17) of each of the lower cartridges, of a stack of cartridges, is shown. In this alternative configuration, the sealing recesses each have a cap (111) for the nozzles (17) of a lower one of the cartridges. Each of the sealing caps (111) are held or retained within a recess (113) in the adjacent cartridge body (115). The sealing caps (111) are held within the adjacent cartridge body (115) such that they are removed from the nozzles (17) as each cartridge body (115) is separated from the adjacent cartridge body (115).

Figure 15:
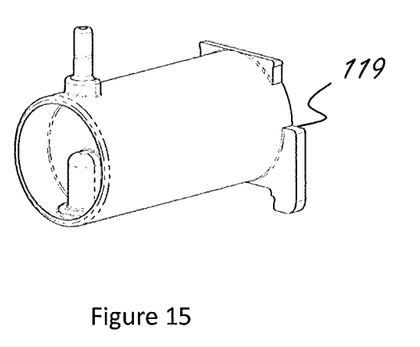
FIG. 15 is a perspective view of an alternative dosing cartridge.

FIG. 15 illustrates a particular alternative embodiment of the cartridge. It is configured for use in a modified dispenser gun where there is no top moving slide (55) for retaining the cartridge in the magazine as described above, but rather where the gun has a side moving slide or slides (not shown) which engage shoulders (119) at the rearward end of the cartridge.

Figure 16:
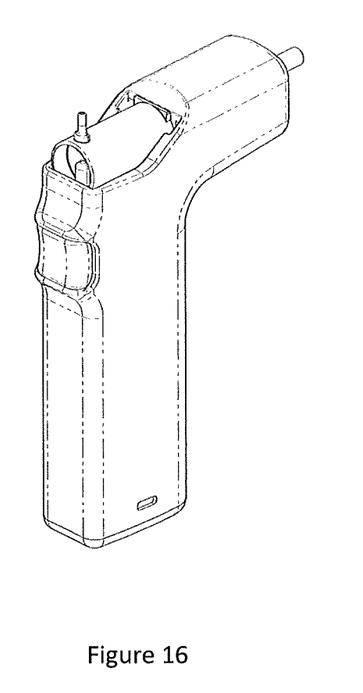
FIG. 16 is a perspective view of an alternative dispenser gun loaded with a stack of cartridges, powered other than by hand.

Referring to FIG. 16, in a further embodiment of the invention the cartridges are in a stack as described above, but the dispenser gun is other not hand powered. The gun rather relies on pneumatic (eg compressed air) or electrical (eg battery) power to drive the plunger.

In summary, it will be understood that some embodiments of the invention enable a dosing cartridge and a dispenser gun combination which:
  facilitates reduction in the total volume of plastic packaging used to store the formulations, ie because one gun may have multiple cartridges, while still ensuring each dose is still in its own separate package,
  is simple to load, use and operate with a very comfortable ergonomic design,
  does not require the user to undertake secondary actions to remove the cap of each cartridge; this procedure is automatically accomplished at the same time as the user is delivering the dose of the cartridge preceding the dose from which the cap is being removed, and/or
  enables the packaging and delivery of dual product formulations from a single cartridge.

However, it should be understood that these advantages may not apply to every embodiment of the invention. It should not be inferred or otherwise taken that the invention per se is limited to embodiments which have such advantages.

While aspects and embodiments of the invention have been described by way of example only and it should be appreciated that modifications and improvements may be made without departing from the scope of the following claims.

The invention claimed is:

1. A dosing apparatus for dispensing therapeutic and/or preventative product into an orifice of an animal, comprising:
  a plurality of interlocking cartridges arranged in a stack, each cartridge containing at least one product, and each cartridge including:
    a body with a cavity holding at least one product to be dosed,
    a nozzle which is in communication with the cavity and which is configured for channelling the product to an orifice of an animal, the nozzle being disposed on the top of the body whereby product is dispensed upwardly from the dosing apparatus to the orifice of the animal,
    at least one piston configured to push product from the cavity, and
    a recess which is adapted to receive and provide a cover for the nozzle of an identical or similar cartridge; and
  a dispenser for holding the cartridges and for dispensing product from each cartridge, one after the other, the dispenser including:
    a magazine adapted to receive the stack of cartridges, and
    a plunger arranged to drive the piston (s) of one of the cartridges;
  wherein the nozzle comprises a cannula without a needle;
  wherein the nozzle comprises a tubular section sized to fit within the teat orifice of a dairy cow for mastitis prevention and treatment; and
  wherein the nozzle is disposed at an angle relative to the body of 70°-90°.

2. The dosing apparatus according to claim 1, wherein the recess seals the nozzle of the second mentioned cartridge.

3. The dosing apparatus according to claim 2, wherein the nozzle of the second mentioned cartridge includes a resilient collar section at a base thereof which is in sealing contact with a complimentary shaped portion of the recess of the first mentioned cartridge.

4. The dosing apparatus according to claim 1, wherein the angle is 90°.

5. The dosing apparatus according to claim 1, wherein the cavity is cylindrical.

6. The dosing apparatus according to claim 1, wherein each cartridge has a first piston configured to expel the product from its cavity, and a second piston configured to expel a second product from the cavity.

7. The dosing apparatus according to claim 6, wherein each cartridge is configured to expel the first mentioned product through the nozzle, and: only after that, to expel the second mentioned product such that it flows past the first piston and exits the cartridge via the nozzle.

8. The dosing apparatus according to claim 7, wherein the cavity of each cartridge is configured to allow the second product to flow past the first piston when the first piston has travelled to the limit of its range of travel after dispensing the first mentioned product.

9. The dosing apparatus according to claim 8, wherein the cavity of each cartridge includes a section having a greater cross sectional area at the location where the first piston sits when it has travelled to the limit of its range after dispensing the first mentioned product.

10. The dosing apparatus according to claim 8, wherein the cavity of each cartridge includes a section having a reduced radius at a location where the first piston sits when it has travelled to the limit of its range of travel after dispensing the first mentioned product.

11. The dosing apparatus according to claim 6, wherein the first piston of each cartridge has a uni-directional seal which is configured to prevent the first mentioned product from travelling past the first piston and toward the second piston and to allow the second mentioned product to flow past the first piston.

12. The dosing apparatus according to claim 1, wherein the dispenser is a hand held dispenser gun.

13. The dosing apparatus according to claim 1, wherein the magazine has a spring which biases the cartridges towards a breach of the dispenser for engaging the plunger.

14. The dosing apparatus according to claim 1, wherein the dispenser incorporates a squeeze handle for powering movement of the plunger and has a spring for biasing the handle to a non-squeezed disposition.

15. The dosing apparatus according to claim 13, wherein the dispenser has a slide which prevents one of the cartridges, which is in the breach, from being released from the dispenser until that cartridge has had its product contents expelled via its nozzle.

16. The dosing apparatus according to claim 15, formed such that the slide is automatically withdrawn during a reloading sequence of the dispenser.

17. The dosing apparatus according to claim 16, having a blade which moves with and as part of, the plunger to push between the cartridges and assist in separating them when one of the cartridges in the breach has been used.

18. The dosing apparatus according to claim 1, having a hand squeeze mechanism configured to push the plunger to dispense the product from the cartridges one after the other.

19. The dosing apparatus according to claim 1, wherein the plunger is:
pneumatically powered;
electrically powered; or
hydraulically powered.

20. A dosing apparatus for dispensing a mastitis therapeutic and/or preventative product into a teat orifice of a dairy cow, comprising:
(a) a plurality of interlocking cartridges arranged in a stack, each cart ride containing at least one mastitis therapeutic and/or preventative product, and each cartridge including:
   (i) a body with a cavity holding at least one product to be dosed,
   (ii) a tubular nozzle, sized to fit within a teat orifice of a cow, which is in communication with the cavity and which is configured for channelling the product to a teat orifice of a cow, the nozzle being disposed on the top of the body whereby product is dispensed upwardly from the dosing apparatus to the teat orifice of the cow, the nozzle being disposed at and angle relative to the body of 90 degrees,
   (iii) at least one piston configured to push product from the cavity, and
   (iv) a recess disposed on the bottom of the body which is adapted to receive and provide a cover for the nozzle of an identical cartridge in the stack of cartridges; and
(b) a dispenser for holding the cartridges and for dispensing product from each cartridge, one after the other, the dispenser including:
   (i) a vertically oriented magazine adapted to receive the stack of cartridges, the magazine having a breach at its top end for exposing the nozzle of a cartridge for contact with the teat orifice of a cow, and
   (ii) a plunger arranged to drive the piston(s) of one of the cartridges.

21. A needle-less dosing apparatus for dispensing a mastitis therapeutic and/or preventative product into a teat orifice of a dairy cow, comprising:
(a) a plurality of interlocking cartridges arranged in a stack, each cartridge containing at least one mastitis therapeutic and/or preventative product, and each cartridge including:
   (i) a body with a cavity holding at least one product to be dosed,
   (ii) a needle-less, tubular nozzle, sized to fit within a teat orifice of a cow, which is in communication with the cavity and which is configured for channeling the product to a teat orifice of a cow, the nozzle being disposed on the top of the body whereby product is dispensed upwardly from the dosing apparatus to the teat orifice of the cow, the nozzle being disposed at and angle relative to the body of 90 degrees,
   (iii) at least one piston configured to push product from the cavity, and
   (iv) a recess disposed on the bottom of the body which is adapted to receive and provide a cover for the nozzle of an identical cartridge in the stack of cartridges; and
(b) a dispenser for holding the cartridges and for dispensing product from each cartridge, one after the other, the dispenser including:
   (i) a vertically oriented magazine adapted to receive the stack of cartridges, the magazine having a breach at its top end for exposing the nozzle of a cartridge for contact with the teat orifice of a cow, the magazine further having a spring disposed at its bottom which biases the stack of cartridges towards the breach,
   (ii) plunger arranged to drive the at least one piston of one of the cartridges, the plunger engaging the cartridge at the breach, and
   (iii) a slide which prevents the cartridge which is in the breach, from being released from the dispenser until that cartridge has had its product contents expelled via its nozzle.

* * * * *